United States Patent [19]

Kawauchi

[11] Patent Number: 4,460,576

[45] Date of Patent: Jul. 17, 1984

[54] PEPTIDE AND HORMONE AGENT CONTAINING THE SAME AS EFFECTIVE INGREDIENT

[75] Inventor: Hiroshi Kawauchi, Iwate, Japan

[73] Assignees: Kaken Pharmaceutical Co., Ltd., Tokyo; Suntory Limited, Osaka, both of Japan

[21] Appl. No.: 463,604

[22] Filed: Feb. 3, 1983

[30] Foreign Application Priority Data

Feb. 3, 1982 [JP] Japan .................................. 57-16691

[51] Int. Cl.³ ...................... C07C 103/52; A61K 37/02
[52] U.S. Cl. .............................. 424/177; 260/112.5 R
[58] Field of Search .................. 260/112.5 R; 424/177

[56] References Cited

U.S. PATENT DOCUMENTS

| | | | |
|---|---|---|---|
| 3,664,925 | 5/1972 | Sonenberg et al. | 424/177 |
| 4,253,998 | 3/1981 | Sarantakis | 424/177 |
| 4,372,884 | 2/1983 | Brown et al. | 260/112.5 S |

Primary Examiner—Delbert R. Phillips
Assistant Examiner—F. T. Moezie
Attorney, Agent, or Firm—Armstrong, Nikaido, Marmelstein & Kubovcik

[57] ABSTRACT

A peptide having the structural formula (I):

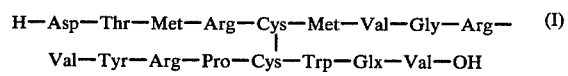

wherein Glx is Glu or Gln, and the following physical properties:
(1) Ultraviolet Absorption Spectrum: Max 280 nm.,
(2) Ehrlich reaction, Sakaguchi reaction and Pauly's reaction: positive,
(3) Basic,
(4) Soluble in water, methanol and acetic acid, slightly soluble in ethyl acetate, butyl acetate, ethyl ether, hexane, petroleum ether, benzene and chloroform, and
(5) white powder has a specifically GH-releasing effect and no species-specificity.

The peptide is useful not only for human dwarfism and wound repair but also for stimulating a growth of domestic animal.

6 Claims, 9 Drawing Figures

PEPTIDE AND HORMONE AGENT CONTAINING THE SAME AS EFFECTIVE INGREDIENT

BACKGROUND OF THE INVENTION

The present invention relates to a novel peptide and the salt thereof having a growth hormone (hereinafter referred to as "GH")-releasing effect and a hormone agent containing the same as an effective ingredient.

GH is one of the hormones of the pituitary being capable of promoting growth, effecting directly or indirectly on somatic cells to stimulate overall protein synthesis in an animal body and stimulating release of free fatty acids to increase energy availability. Though GH has been applied for therapy of Dwarfism, it can be much expected from the above-mentioned GH effect that the GH is further applied for wound repair requiring activation of somatic cells.

Unlike, insulin, however, GH having high species-specificities cannot be applied for a human body if it is extracted from bovine or porcine pituitaries. Besides, human GH being a single polypeptide consisting of 191 amino acids and having a large molecular weight (about 22,000) cannot be synthesized by an organic synthesis. Therefore, GH has been extracted from pituitaries of the same kind of animals, but is very short in supply for therapy of Dwarfism.

GH as well as thyroid-stimulating hormone (hereinafter referred to as "TSH"), luteinizing hormone (hereinafter referred to as "LH"), and the like are under the control of the hypothalamus. It has been found that secretion of each pituitary hormone is specifically stimulated by the corresponding releasing hormone (hereinafter referred to as "RH") secreted from hypothalamus.

For instance, thyrotropic releasing hormone (hereinafter referred to as "TRH") stimulating the secretion of TSH and luteinizing hormone-releasing hormone (hereinafter referred to as "LH—RH") stimulating the secretion of LH have been isolated and identified.

As to growth hormone-releasing hormone (hereinafter referred to as "GH—RH") stimulating the secretion of GH, though it was suggested that GH—RH was a peptide consisting of ten amino acids and isolated from porcine hypothalamic tissues by Shary, 1971, it has been confirmed that the above peptide is foreign to GH—RH as a result of later study. Since then, GH—RH has not been found out yet in any animals.

On the other hand, it has been found that GH is somewhat released in a non-specific manner by utilizing some substances such as arginine, glucagone and TRH. In addition, though they say that prostaglandine E, theophylline, cyclic-adenyl acid, and the like have GH-releasing effect, the effecting manner is apparently non-specific in the light of principle. Further, though it is considered that certain neurotransmitting peptides have somewhat GH-releasing effect, the effecting manner seems not to be specific.

On the other hand, it has been confirmed that RH in the hypothalamus has no species-specificity in accordance with the study of TRH or LH—RH.

As a result of extensive study on the problems as above, it has now been found that a novel peptide deriving from the hypothalamus can be isolated from an extract of salmon pituitaries and the thus obtained peptide has a specifically GH-releasing effect on foreign animals.

SUMMARY OF THE INVENTION

In accordance with the present invention, there can be provided a peptide or the salt thereof having the structural formula (I):

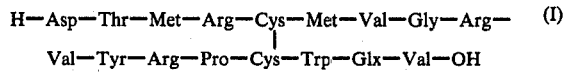

wherein Glx is Glu or Gln, and the following physical properties:

(1) Ultraviolet Absorption Sepctrum: Max 280 nm.
(2) Ehrlich reaction, Sakaguchi reaction and Pauly's reaction: positive,
(3) Basic,
(4) Soluble in water, methanol and acetic acid, slightly soluble in ethyl acetate, butyl acetate, ethyl ether, hexane, petroleum ether, benzene and chloroform, and
(5) white powder.

In accordance with the present invention, there can be also provided a hormone agent containing the above peptide or the salt thereof as an effective ingredient.

DETAILED DESCRIPTION

Figure 1:
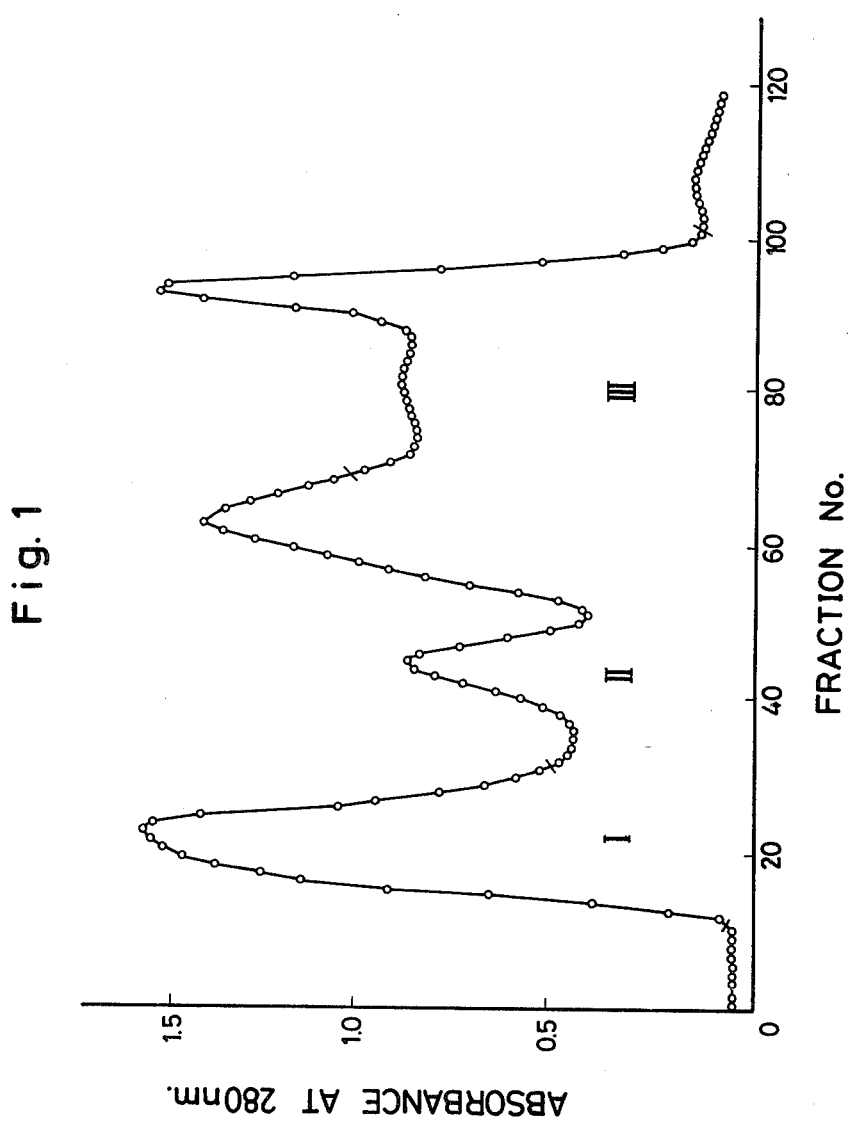
FIG. 1 represents a column chromatogram obtained by means of a gel filtration column chromatography in Example 1.

In the instant specification the following abbreviations represent, respectively, the following amino acids.
Asp: Aspartic acid
Thr: Threonine
Met: Methionine
Arg: Arginine
Cys: ½ Cystine
Val: Valine
Tyr: Tyrosine
Pro: Proline
Trp: Tryptophan
Gln: Glutamine
Glu: Glutamic acid
Asx: Aspartic acid or Asparagine
Glx: Glutamic acid or Glutamine Examples of the salt of the peptide of the present invention are, for instance, acid addition salts with hydrochloric acid, sulfuric acid, acetic acid, lactic acid, citric acid, oxalic acid, fumaric acid, maleic acid, and the like.

The peptide of the present invention can be obtained by extracting salmon pituitaries. A salmon hypothalamus alone cannot be completely isolated because a salmon hypothalamus is penetrated into pituitary unlike that of a mammalian. Therefore, the extraction should be conducted out of an isolated mixture of both a pituitary and a hypothalamus. Accordingly, in the instant specification, "salmon pituitary" means a pituitary containing a hypothalamus.

The peptide of the present invention can be obtained by extracting freshly lyophilized salmon pituitaries with HCl-acetone, salting out the extracts, isolating the desired peptide by means of a gel filtration chromatography and an ion exchange chromatography, and then conducting a purification with a HPLC. In that case, the thus obtained peptide is a GH—RH having the structural formula (I) in which Glx is Glu. The obtained peptide can be easily converted to a form of the acid addition salt by lyophilizing or crystallizing it after treating with an inorganic acid such as hydrochloric acid.

On the other hand, as a result of extensive study of synthesizing such a kind of peptide, it has now been found that the peptide of the present invention can by synthesized by a peptide synthesis technique.

In the present invention, the peptide of the present invention can be synthesized on the basis of the structure of the above GH—RH obtained from salmon pituitaries. In that case, [Gln$^{16}$]—GH—RH can be synthesized when Gln is employed as Glx while [Glu$^{16}$]—GH—RH can be synthesized when Glu is employed as Glx. With respect to manners to be employed for the above synthesis, Haruaki Yajima and Syunpei Sakakibara (Tanpakushitsu to Kagaku (Protein Chemistry), SEIKAGAKU JIKKEN KOZA (Experimental Biochemistry) (I), 4, p. 208-495 (1977) edited by Japanese Biochemical Soc. and publised by Kabushiki Kaisha Tokyo Kagaku Dohjin) and Nobuo Izumiya et al (PEPTIDE GOHSEI (SYNTHESIS) (1975) published by Maruzen Kabushiki Kaisha) may be referred.

The peptide of the present invention is a GH—RH having a specifically GH-releasing effect and no species-specificity. Therefore, the GH—RH agent containing the peptide of the present invention as an effective ingredient can be used not only for therapy of human dwarfism and wound repair, but also for stimulating a growth of domestic animal.

The peptide of the present invention, like other physiologically active peptides, has specific receptors in a body and causes specific reactions by specifically effecting on the receptors. GH—RH can release GH in a pituitary having specific receptors but it has no effect on the other tissues having no specific receptors.

In addition, the peptide of the present invention consisting of L-amino acids alone is successively digested with various proteases and its effect cannot be maintained.

On the other hand, the peptide having such a degree of molecular weight (about 2,000) has no antigenicity and causes neither antibody production nor anaphylaxy shock even if administration is repeated. The peptide has no toxicity.

The peptide of the present invention shows the effect in an extremely low dosage of about ng./kg. order being less than that of GH itself on the basis of the amount of the effective ingredient. The effect is increased in proportion to dosage, and the dosage can be amounted to mg./kg. order. The preferred dosage is usually from 1 ng./kg. to 10 mg./kg.

The peptide of the present invention is preferably administered by means of an injection such as intravenous injection, intramuscular injection, subcutaneous injection, and the like, usually employed for peptide agents. In case of administrating the peptide of the present invention orally, the peptide is digested in digestive organs and converted to inactive form. In that case, however, it can be used in some preparation forms such as microcapsule packed in liposome being not digested in organs. Further, the peptide of the present invention is also administered from mucosa other than digestive organs, such as rectum, sublingual, nose, and the like. In that case, it can be used in a variety of preparation forms such as suppository, sublingual tablet, rhinologic spray. Examples of excipients are usual ones with which the peptide of the present invention is not digested.

The present invention is more specifically described and explained by means of the following Examples. It is to be understood that the present invention is not limited to the Examples and various changes and modifications may be made in the invention without departing from the spirit and scope thereof.

EXAMPLE 1

Figure 2:
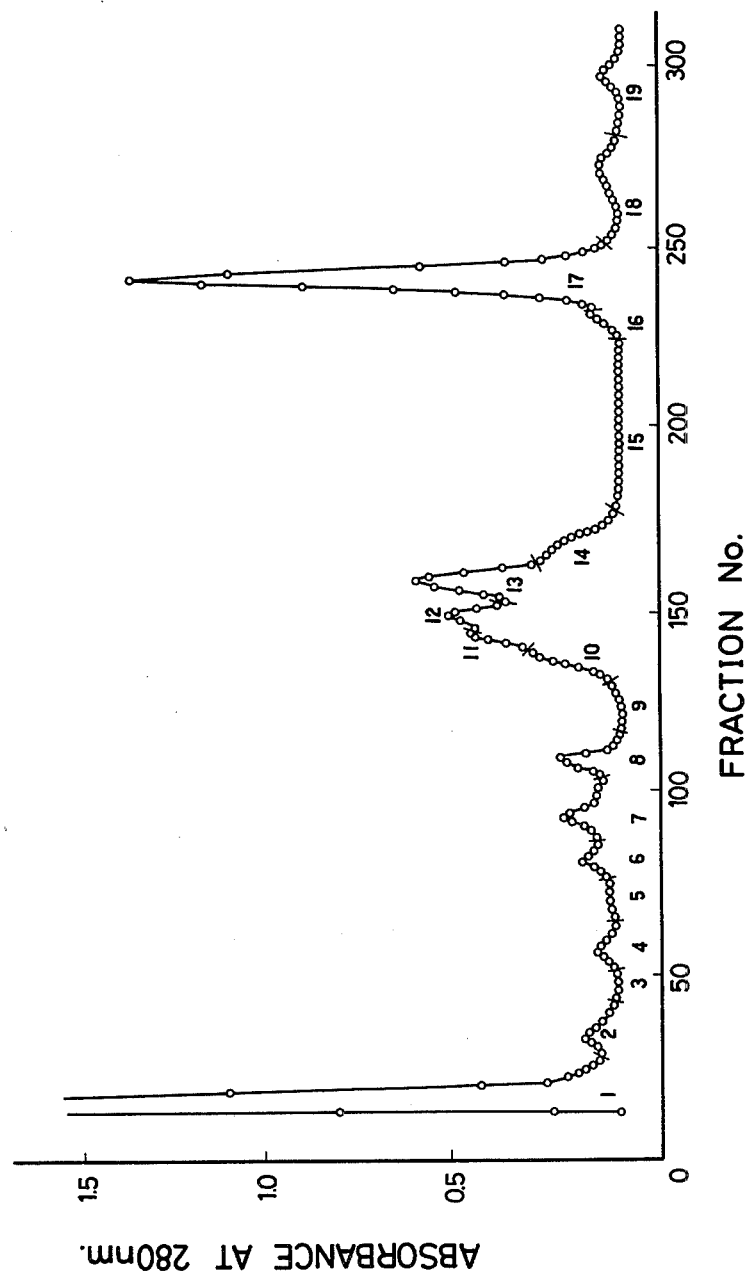
FIG. 2 represents an ion-exchange chromatogram obtained by means of an ion-exchange chromatography in Example 1.

About 100 g. of fresh pituitary obtained from female while salmons (*Oncorhynchus keta*) was extracted with 400 ml. of 35% hydrochloric acid-acetone mixed liquor at a ratio of 1:28 and then 280 ml. of 80% acetone. The each extract was combined and added to 10 l. of acetone with stirring to give 3.0 g. of acidic acetone precipitate. The obtained precipitate was added to 90 ml. of water, adjusted to pH 3, and if necessary, readjusted with 0.1N sodium hydroxide or 0.1N hydrochloric acid. And then 10 ml. of saturated NaCl solution was added for salting out. After centrifuging the obtained precipitate, the resulting supernatant was chromatographed on a column (5.5×68 cm.) of Sephadex G 25 (M). Elution was effected with 0.1N acetic acid (fraction amount: 10 ml./fraction). The obtained chromatogram is shown in FIG. 1. The fraction (III) shown in FIG. 1 having a volume of 320 ml. was desalted with UM-2 membrane filter (made by Amicon Co.), and then lyophilized to give 139 mg. of white powder. The resulting powder was further chromatographed on an ion-exchange column (1.6×63.0 cm.) of CM-cellulose. Elution was effected by means of a gradient obtained by employing 500 ml. of 0.01M ammonium acetate buffer, pH 4.6, while adding 0.1M ammonium acetate buffer, pH 7.0, dropwise. The resulting chromatogram is shown in FIG. 2. The fraction (8) shown in FIG. 2 having a volume of 110 ml. was lyophilized to give 1.5 mg. of crude GH—RH.

The obtained crude GH—RH was further chromatographed on a column (0.4×2.5 cm.) of HPLC (fine packcyl C 18 made by Nippon Bunko Kogyo Kabushiki Kaisha) being equilibrated with 0.01M ammonium acetate, pH 5.0.

Figure 3:
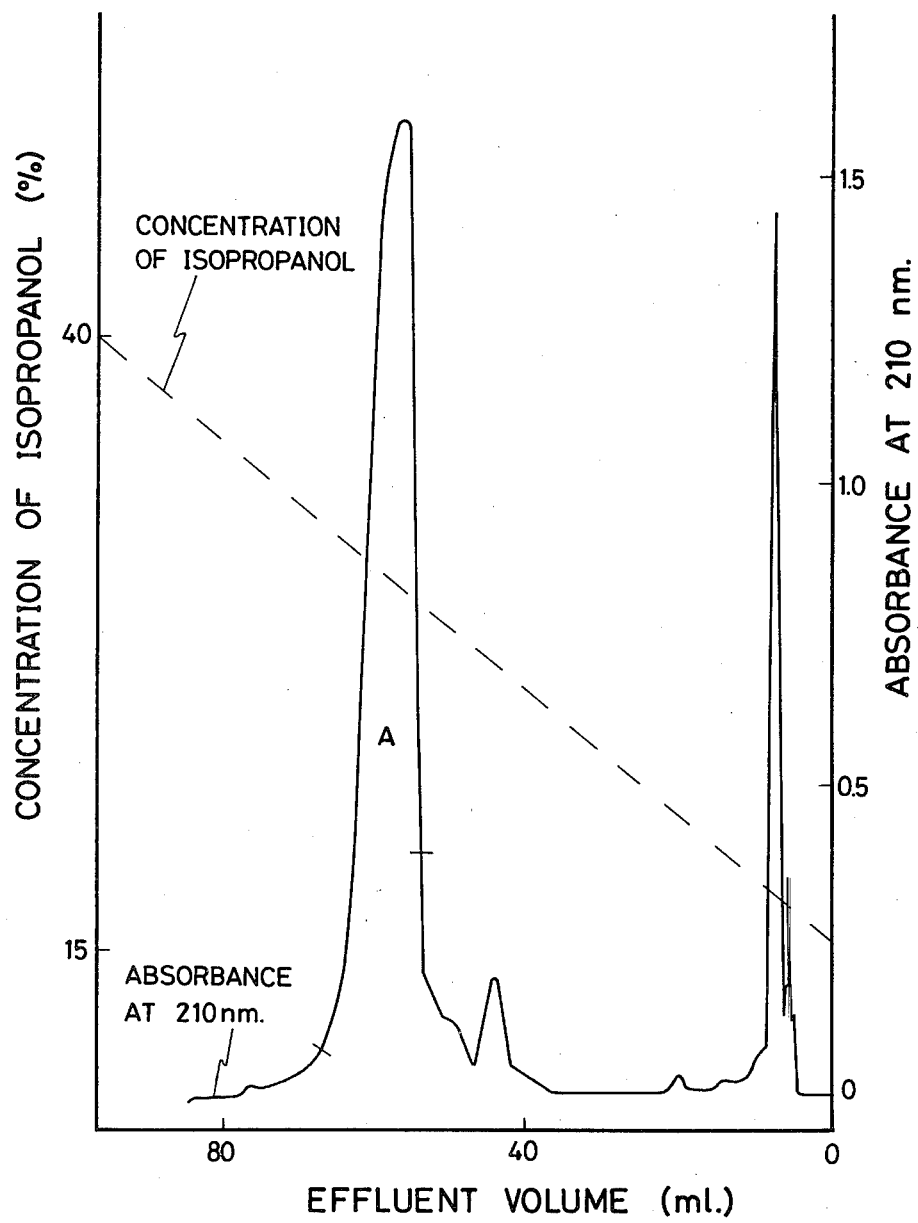
FIG. 3 represents an elution curve obtained by means of a reversed phase high-pressure liquid chromatography (hereinafter referred to as "HPLC") in Example 1.

Elution was effected by means of a linear gradient of isopropanol (concentration of 15% to 45%) in a constant level device at a flow rate of 1 ml./minute and column temperature of room temperature and the column effluent was collected in 1 ml.-fractions. The resulting elution curve is shown in FIG. 3. The fraction (A) shown in FIG. 3 having a volume of 13.3 ml. was lyophilized to give 0.51 mg. of peptide of the present invention having high purity of 99% or more.

The physical properties of the obtained basic peptide were as follows:

Appearance: white powder

Molecular Weight: 500 to 3000 (determined by gel filtration)

Color Reactions: Ehrlich reaction (+), Sakaguchi reaction (+), Pauly's reaction (+)

Figure 4:
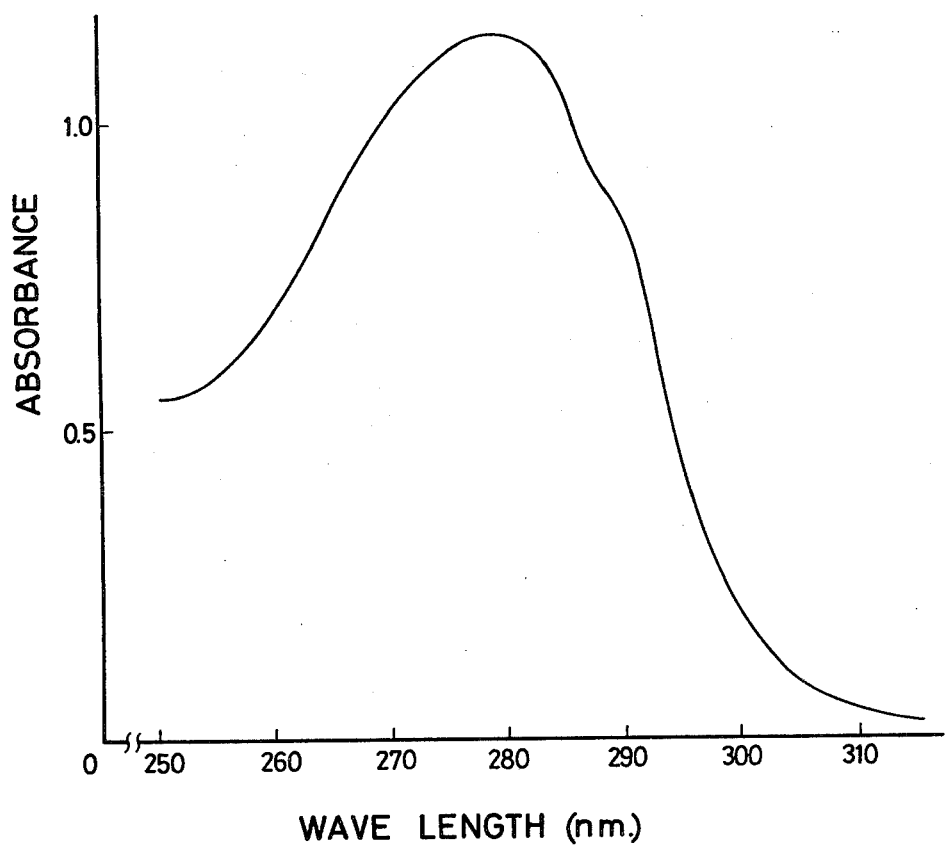
FIG. 4 represents an ultraviolet absorption spectrum chart of the peptide of the present invention.

Solubility: soluble in water, methanol and acetic acid; slightly souble in ethyl acetate, butyl acetate, ethyl ether, petroleum ether, hexane, benzene and chloroform Ultraviolet Absorption Spectrum (in 0.1N acetic acid; a concentration of 0.166 mM): shown in FIG. 4.

In 5 ml. of distilled water was dissolved 500 µg. of the above peptide, converted to acid with several drops of 0.1N hydrochloric acid and lyophilized to give 500 µg. of hydrochloride of the peptide of the present invention.

Amino acid compositions and amino acid sequences of the peptide obtained in Example 1 were determined according to the following Analytical Examples 1 to 8.

ANALYTICAL EXAMPLE 1

[Amino acid compositions analyzed after acid hydrolysis]

Amino acid analysis was carried out on LKB 4400 amino acid autoanalyzer (LKB Biochrom Co., Ltd.) after hydrolysing the peptide obtained in Example 1 in 6N HCl at 110° C. for 18 hours.

The results are shown as follows:

| Amino acid | Found (molar ratio) | Calcd. (molar ratio) |
|---|---|---|
| Asp | 1.0 | 1 |
| Thr | 1.0 | 1 |
| Glx | 1.1 | 1 |
| Pro | 1.2 | 1 |
| Gly | 1.1 | 1 |
| Cys | 1.9 | 2 |
| Val | 3.0 | 3 |
| Met | 2.0 | 2 |
| Tyr | 0.8 | 1 |
| Arg | 2.5 | 3 |
| Trp | 1.2 | 1 |

The found value of Cys was determined by means of performic acid oxidation.

ANALYTICAL EXAMPLE 2

[N-terminal amino acid]

The N-terminal amino acid of the peptide obtained in Example 1 was determined according to Dansyl method (see Gray et al, Biochemica. J., 89, p.379 (1963)) and proved to be Asx.

ANALYTICAL EXAMPLE 3

[C-terminal amino acid]

The C-terminal amino acid of the peptide obtained in Example 1 was determined according to a Hydrazinolysis method (see Akabori et al, Bulletin Chemical Soc. Japan 25, p.214 (1952)) and proved to be Val.

From the Analytical Examples 1 to 3, it was found that the peptide of the present invention is a heptadecapeptide consisting of different eleven kinds of seventeen amino acids having a calculated molecular weight of 2,211 as a trihydrochloride and N-terminal Asx and C-terminal Val.

ANALYTICAL EXAMPLE 4

[Amino acid sequence (1)]

With employing 66 µg. (about 30 nmoles) of the carboxymethylated peptide obtained in Example 1, amino acid sequence was determined from the N-terminal residue according to Edman-Dansyl method (see Hartley et al, Biochimica. Biophysica. Acta., 21, p.58 (1956)). The result is as follows:

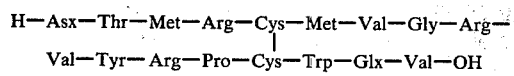

ANALYTICAL EXAMPLE 5

[Amino acid sequence (2)]

With employing 88 µg. (about 40 nmoles) of the carboxymethylated peptide obtained in Example, the amino acid sequence was determined from the N-terminal residue according to a Fluorescein-isocyanate method (see Muramoto et al, Agricultural and Biological Chemistry, 44, p.1559 to 1563 (1978)). The result is as follows:

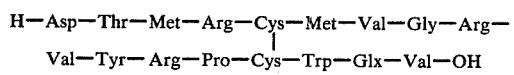

The above Fluorescein-isocyanate method by Muramoto et al is a particularly reliable method for determining an amino acid sequence with a small amount of samples.

ANALYTICAL EXAMPLE 6

[Carboxypeptidase Y digestion]

To 0.2M N-ethylmorpholine acetate buffer, pH 8.0, containing carboxypeptidase Y (Oriental Yeast Company Limited) was added 10 nmols of the peptide obtained in Example 1, the reaction mixture was incubated at 37° C. Carboxypeptidase Y:substrate=1:60 (by weight). The amino acid compositions of the digest obtained in 1 hr. and 5 hrs. were determined. Two of them are shown as follows:

| Amino acid | 1 hr. (molar ratio) | 5 hrs. (molar ratio) |
|---|---|---|
| Val | 1.0 | 1.0 |
| Glu | 0.2 | 0.5 |

From the results, together with Analytical Example 3, the C-terminal sequence was proved to be —Glu—Val—OH.

From Analytical Examples 1 to 6, the complete amino acid sequence of the peptide of the present invention was elucidated as follows:

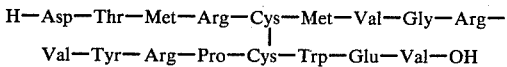

Further, the peptide of the present invention was digested with chymotrypsin or trypsin, and then the amino acid compositions, N-terminal amino acid and amino acid sequence of the obtained digest were investigated according to the following Analytical Examples 7 and 8 in order to confirm the complete amino acid sequence.

ANALYTICAL EXAMPLE 7

[Chymotrypsin digestion]

Figure 5:
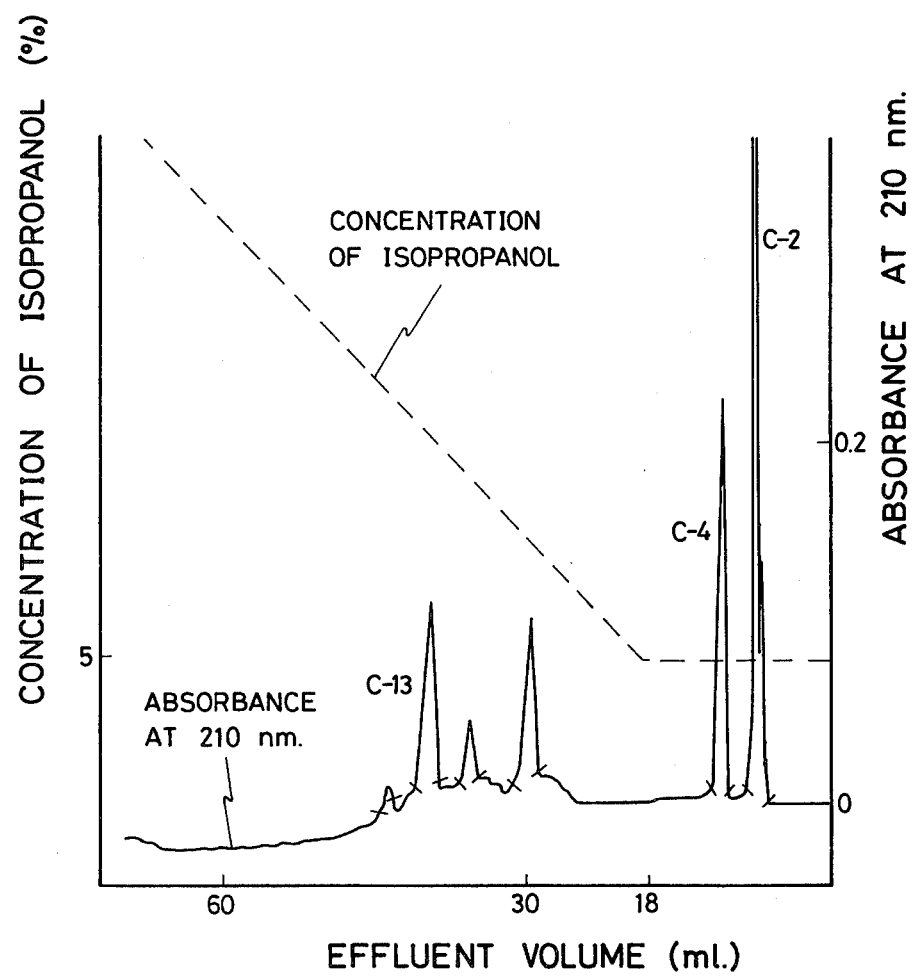
FIG. 5 and FIG. 6 represent, respectively, an elution curve obtained by means of a HPLC in Analytical Examples 7 and 8.

To 0.2M ammonium acetate buffer, pH 8.0, containing chymotrypsin was added 110 μg. of the peptide obtained in Example 1, and the reaction mixture was incubated for one hour at 37° C. Chymotrypsin:substrate was 1:250 by weight. The obtained digest was subsequently analyzed by means of a HPLC performed in the same manner as in Example 1 except that elution was effected with 5 to 50% isopropanol. The resulting elution curve is shown in FIG. 5. The fractions (C-2), (C-4) and (C-13) shown in FIG. 5 were analyzed, respectively, in the same manner as in Analytical Examples 1 and 2, and the amino acid compositions and the N-terminal amino acid thereof were determined. The results are as follows:

| Amino acid | Found (molar ratio) | Calcd. (molar ratio) |
|---|---|---|
| Fraction (C-2) | | |
| Asx | 1.0 | 1 |
| Thr | 1.0 | 1 |
| Met | 1.0 | 1 |
| Arg | 0.6 | 1 |
| N—terminal amino acid: Asx | | |
| Fraction (C-4) | | |
| Gly | 1.0 | 1 |
| Val | 2.2 | 2 |
| Tyr | 0.9 | 1 |
| Arg | 0.8 | 1 |
| N—terminal amino acid: Val | | |
| Fraction (C-13) | | |
| Glx | 1.0 | 1 |
| Pro | 1.2 | 1 |
| Cys | 1.8 | 2 |
| Val | 1.0 | 1 |
| Met | 0.9 | 1 |
| Arg | 1.3 | 1 |
| Trp | + (detected and confirmed by Ehrlich reagent) | |
| N—terminal amino acid: Arg | | |

The fractions (C-2), (C-4) and (C-13) were subsequently analyzed, respectively, in the same manner as in Analytical Example 4 to determine the amino acid sequences. In that case, the fractions (C-2) and (C-4) were analyzed as they were and the fraction (C-13) was analyzed after carboxymethylation. The identification of Trp was carried out by means of Edman-Dansyl method in which Trp is determined as DNS-Trp by means of hydrolysis with thioglycolic acid. Cys was determined as DNS-Cm-Cys in the same manner as above. The results are shown as follows:

Fraction (C-2)
H—Asx—Thr—Met—Arg—OH
Fraction (C-4)
H—Val—Gly—Arg—Val—Tyr—OH
Fraction (C-13)
H—Cys—Met—OH  H—Arg—Pro—Cys—Trp—Glx—Val—OH
                    |_____|

ANALYTICAL EXAMPLE 8

[Trypsin digestion]

Figure 6:
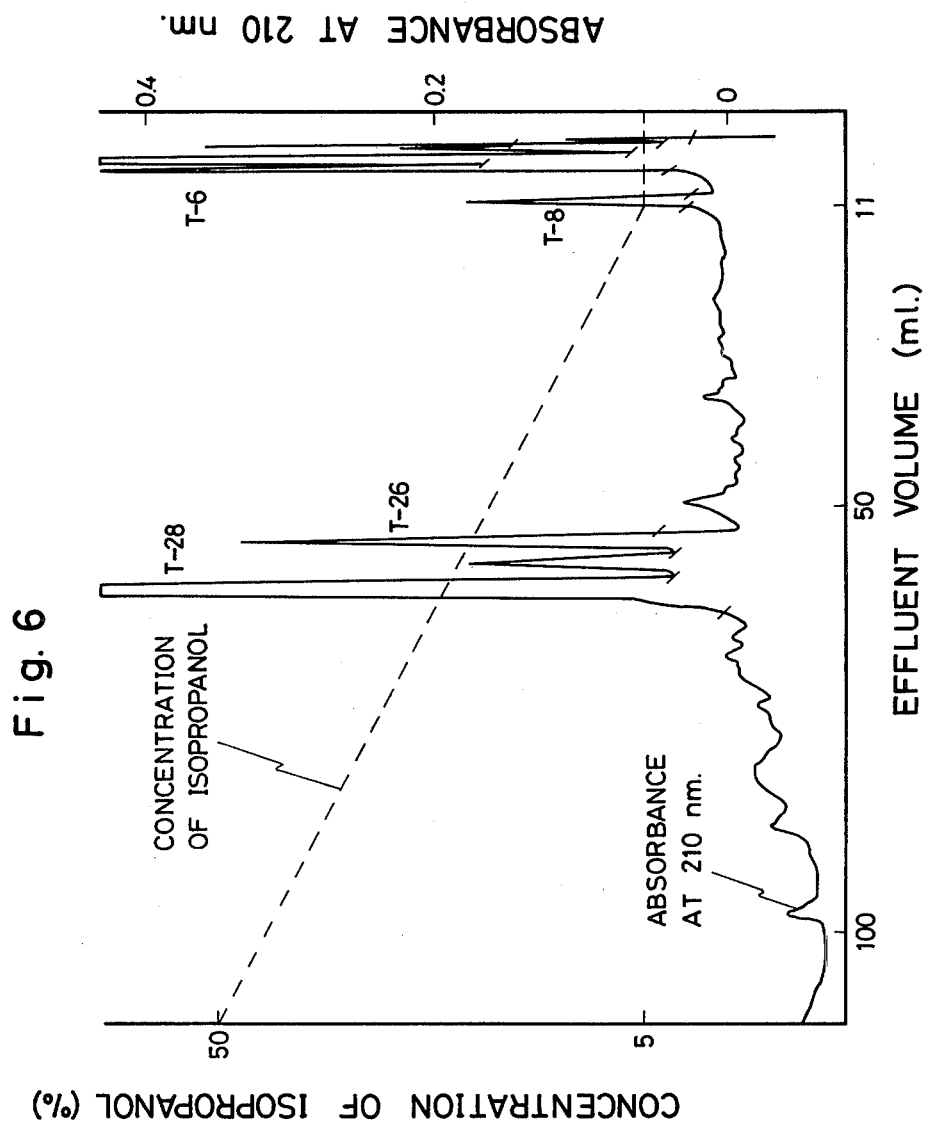

To 0.2M ammonium acetate buffer, pH 8.0, containing trypsin was added 88 μg, (about 30 nmoles) of the peptide obtained in Example 1, and the reaction mixture was incubated for four hours at 37° C. Trypsin:substrate was 1:50 by weight. The obtained digest was subsequently analyzed by means of a HPLC performed in the same manner as in Example 1 except that elution was effected with 5 to 50% isopropanol. The resulting elution curve is shown in FIG. 6. The fractions (T-6), (T-8), (T-26) and (T-28) shown in FIG. 6 were analyzed, respectively, in the same manner as in Analytical Examples 1 and 2, and the amino acid compositions and the N-terminal amino acid thereof were determined. The results are as follows:

| Amino acid | Found (molar ratio) | Calcd. (molar ratio) |
|---|---|---|
| Fraction (T-6) | | |
| Asx | 1.0 | 1 |
| Thr | 0.9 | 1 |
| Met | 1.0 | 1 |
| Arg | 1.0 | 1 |
| N—terminal amino acid: Asx | | |
| Fraction (T-8) | | |
| Val | 1.3 | 1 |
| Tyr | 1.0 | 1 |
| Arg | 1.0 | 1 |
| N—terminal amino acid: Val | | |
| Fraction (T-26) | | |
| Glx | 0.9 | 1 |
| Pro | 1.3 | 1 |
| Gly | 1.0 | 1 |
| Cys | 1.6 | 2 |
| Val | 1.9 | 2 |
| Met | 1.0 | 1 |
| Arg | 0.9 | 1 |
| Trp | + (detected and confirmed by Ehrlich reagent) | |
| N—terminal amino acid: Pro | | |
| Fraction (T-28) | | |
| Glx | 1.1 | 1 |
| Pro | 1.3 | 1 |
| Gly | 1.3 | 1 |
| Cys | 1.6 | 2 |
| Val | 2.7 | 3 |
| Met | 1.1 | 1 |
| Tyr | 0.8 | 1 |
| Arg | 2.0 | 2 |
| Trp | + (detected and confirmed by Ehrlich reagent) | |
| N—terminal amino acid: Val | | |

The fractions (T-6), (T-8), (T-26) and the (T-28) were subsequently analyzed, respectively, in the same manner as in the Analytical Example 4 to determine the amino acid sequence thereof. In that case, the fractions (T-6), (T-8) and (T-26) were analyzed as they were, and the fraction (T-28) was analyzed after carboxymethylation. The results are as follows:

Fraction (T-6)
H—Asx—Thr—Met—Arg—OH
Fraction (T-8)

-continued

H—Val—Tyr—Arg—OH
Fraction (T-26)

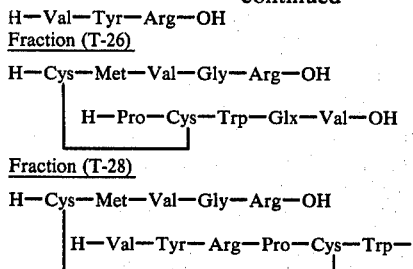

Fraction (T-28)

H—Cys—Met—Val—Gly—Arg—OH
    |
    H—Val—Tyr—Arg—Pro—Cys—Trp—Glx—Val—OH

The results obtained in Analytical Examples 7 and 8 are completely agree with those of Analytical Examples 1 to 6 and it is clear that the determined amino acid sequence should be true.

EXAMPLE 2

[Synthesis of [Gln$^{16}$]—GH—RH]

In the Example 2, the developing solvents employed for a thin layer chromatography are as follows:
R$_{f1}$:(CHCl$_3$:CH$_3$OH:H$_2$O=8:3:1)
R$_{f2}$:(CHCl$_3$:CH$_3$OH:CH$_3$COOH=9:1:0.5)
R$_{f3}$:(CHCl$_3$:CH$_3$OH=9:0.5)
R$_{f4}$:(CHCl$_3$)
R$_{f5}$:(n-(C$_4$H$_9$)OH:CH$_3$COOC$_2$H$_5$:CH$_3$COOH:-H$_2$O=1:1:1:1) and,
the hydrolysis was carried out in 6N HCl with phenol, at 110° C., for 24 hrs. unless otherwise noted.

[Gln$^{16}$]—GH—RH was synthesized by liquid phase method on the basis of the structure of the GH—RH obtained in Example 1. The outline of the synthetic step is as follows:

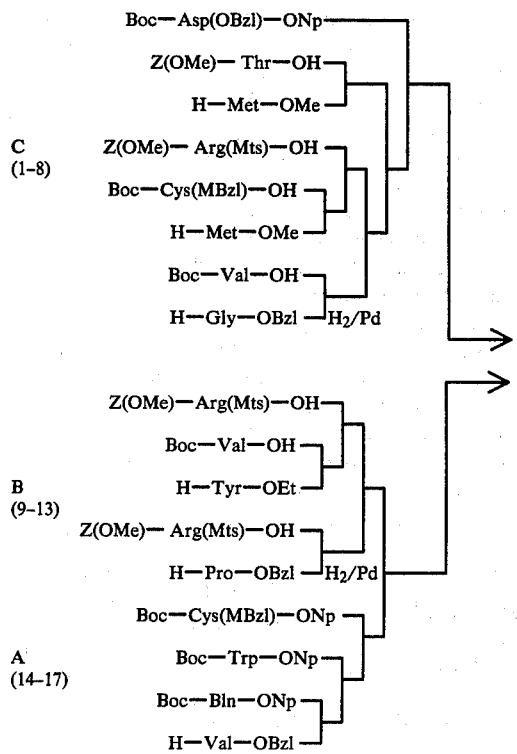

Boc: tertiary-butyloxycarbonyl group
OBzl: O—benzyl group
ONp: O—p-nitrophenol
OMe: O—methyl group
Z(OMe): p-methoxybezyloxycarbonyl group -continued Mts: mesitylene-2-sulfonyl group
MBzl: p-methoxybezyl group
OEt: O—ethyl group (A) Synthesis of Boc—Cys(MBzl)—Trp—Gln—Val—OBzl (14–17 position), M.W.: 845.00
(A-i) Synthesis of Boc—Gln—Val—OBzl (16–17 position), M.W.: 435.508

To 300 ml. of dioxane solution containing 16.4 g. of Boc—Gln—ONp and H—Val—OBzl prepared from 17.5 g. of p-toluenesulfonate and 6.45 ml. of triethylamine (hereinafter referred to as "Et$_3$N") was added 6.45 ml. of Et$_3$N. The obtained reaction mixture was kept at room temperature for 24 hrs. and then concentrated. The residue was dissolved in ethylacetate (hereinafter referred to as "AcOEt"), washed with 5% citric acid, 5% Na$_2$CO$_3$ and NaCl-water, and then dried on Na$_2$SO$_4$. After distilling away AcOEt, the residue was added petroleum ether for crystallization. Recrystallization from AcOEt-ether yielded 16.45 g. (79% of the theoretical amount) of the desired compound.
R$_{f1}$=0.60, R$_{f2}$=0.43.

Elemental analysis for C$_{22}$H$_{33}$N$_3$O$_6$: Calcd. (%): C: 60.67, H: 7.64, N: 9.65, Found (%): C: 60.60, H: 7.54, N: 9.60.

(A-ii) Synthesis of Boc—Trp—Gln—Val—OBzl(-15–17 position, M.W.: 621.714.

To 7.94 ml. of anisole was added 8.00 g. of Boc—Gln—Val—OBzl. The reaction mixture was treated with 30 ml. of trifluoro acetic acid (hereinafter referred to as "TFA") for 60 minutes while cooling with ice and then TFA was distilled away at room temperature. The residue was added to n-hexane, washed by decantation and then dried on KOH. After the obtained oily material was dissolved into 80 ml. of dimethylformamide (hereinafter referred to as "DMF") and neutralized with 2.57 ml. of Et$_3$N, 8.60 g. of Boc—Trp—ONp was added. The reaction mixture was kept at room temperature for 24 hrs. to cause reaction. After distilling away the solvent under 30° C., the residue was dissolved into AcOEt, washed with 5% Na$_2$CO$_3$, 5% citric acid and NaCl-water and then dried on Na$_2$SO$_4$. After distilling away AcOEt, the residue was added to ether for crystallization. Recrystalization form AcOEt-ether yielded 11.0 g. (96% of theoretical amount) of the desired compound.
R$_{f1}$=0.52 R$_{f2}$=0.40.

Elemental analysis for C$_{33}$H$_{43}$N$_5$O$_7$: Calcd. (%): C: 63.75, H: 6.97, N: 11.28, Found (%): C: 63.47, H: 7.00, N: 10.98.

(A-iii) Synthesis of Boc—Cys(MBzl)—Trp—Gln—Val—OBzl (14–17 position), M.W.: 845.00.

To 9.54 g. of Boc—Trp—Gln—Val—OBzl was added 16.56 ml. of 2% ethanedithiol-anisole. The reaction mixture was treated with 50 ml. of TFA under N$_2$ gas for 120 minutes while cooling with ice. After distilling away TFA under 30° C., the residue was added to ether to give a powder and dried on KOH. The obtained white powder was dissolved into 50 ml. of DMF and then 2.36 ml. of Et$_3$N and 7.09 g. of Boc—Cys(MBzl)—ONp were added. The reaction mixture was kept at room temperature for 18 hrs. to cause reaction and neutralized with acetic acid. After distilling away the solvent, the residue was dissolved into AcOEt, washed with 5% Na$_2$CO$_3$, 5% citric acid and NaCl-water and dried on Na$_2$SO$_4$. After distilling away AcOEt, the obtained gel-like material was crushed with ether. Precipitation with methanol-ether was repeated two times to give 10.76 g. (83% of theoretical amount) of the desired compound.

$Rf_1 = 0.57$.

Elemental analysis for $C_{44}H_{56}N_6O_9S$: Calcd. (%): C: 62.54, H: 6.68, N: 9.95, Found (%): C: 62.38, H: 6.74, N: 9.81.

(B) Synthesis of Z(OMe)—Arg(Mts)—Val—Tyr—Arg(Mts)Pro—OH (9-13 positions), M.W.: 707.824.

(B-i) Synthesis of Z(OMe)—Arg(Mts)—Pro—OBzl(-12-13 position).

Into 200 ml. of AcOEt was suspended 9.30 g. of

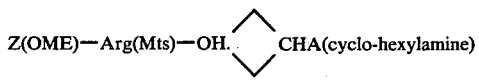

and 3.63 g. of HCl.H—Pro—OBzl while cooling with ice, and then added 3.71 g. of dicyclocarbodiimide (hereinafter referred to as "DCC") while cooling with freezing mixture. The reaction mixture was kept for 24 hrs. to cause reaction under the above conditions. After filtrating out the precipitated dicyclourea, the filtrate was washed with 5% citric acid, 5% $Na_2CO_3$ and NaCl-water and then dried on $Na_2SO_4$. After distilling away AcOEt, n-hexane was added to the residue for crystallization. Recrystallization from AcOEt-petroleum ether yielded 7.80 g. (73% of theoretical amount) of the desired compound.

$Rf_1 = 0.80$.

(B-ii) Synthesis of Boc—Val—Tyr—OEt(10-11 position), M.W.: 408.482.

Into 200 ml. of AcOEt was dissolved 10.86 g. of Boc—Val—OH and H—Tyr—OEt prepared from 12.29 g. of the hydrochloride of H—Tyr—OEt and 7 ml. of $Et_3N$, and then added 11.35 g. of DCC while cooling with freezing mixture. The reaction mixture was kept for 24 hrs. to cause reaction under the above condition. After filtrating out dicyclourea, the filtrate was washed with 5% $Na_2CO_3$, 5% citric acid and NaCl-water and dried on $Na_2SO_4$. After distilling away AcOEt, n-hexane was added to the residue for crystallization. Yield: 20.05 g. (99% of theoretical amount).

$R_{f1} = 0.68$.

Elemental analysis for $C_{19}H_{28}N_2O_5$: Calcd. (%): C: 62.62, H: 7.74, N: 7.69, Found (%): C: 62.80, H: 8.02, N: 7.65.

(B-iii) Synthesis of Z(OMe)—Arg(Mts)—Val—Tyr—OEt (9-11 position), M.W.: 810.944.

To 6.13 g. of Boc—Val—Tyr—OEt was added 8.1 ml. of anisole. The reaction mixture was treated with 32.4 ml. of TFA for 60 minutes while cooling with ice. After distilling away TFA at room temperature, the residue was washed with n-hexane by decantation and dried on KOH. After the obtained oily residue was dissolved into 30 ml. of DMF, 2.1 ml. of $Et_3N$ was added to the solution while cooling with ice. To the obtained reaction mixture in 35 ml. of tetrahydrofuran was added Z(OMe)—Arg(Mts)—OH prepared from 10.23 g. of salt of cyclohexylamine and 17 ml. of 1N hydrochloric acid and mixed acid anhydride prepared from 2.31 ml. of $Et_3N$ and 2.36 ml. of isobutyl chloroformate under anhydrous condition. The reaction mixture was kept at $-15°$ C. for 2 hrs., and then at $0°$ C. for 4 hrs. After distilling away the solvent, the residue was dissolved in AcOEt, washed with 5% citric acid, 5% $Na_2CO_3$ and NaCl-water and dried on $Na_2SO_4$. After distilling away AcOEt, isopropyl ether was added to the residue for crystallization. Furthermore, the obtained crystalline product was dissolved in a small amount of chloroform and chromatographed on a column ($8 \times 5$ cm.) of silica gel in which elution was effected with chloroform:methanol=100:1 to give the crude compound having a $R_{f2}$ of 0.74. After distilling away the solvent, the compound was washed with petroleum ether to give 9.80 g. (81% of theoretical amount) of the desired compound.

$R_{f1} = 0.90$, $R_{f2} = 0.74$, $R_{f3} = 0.47$.

(B-iv) Synthesis of Z(OMe)—Arg(Mts)—Val—Tyr—$N_2H_3$ (9-11 position) M.W.: 796.924.

Into 100 ml. of methanol was dissolved 5.0 g. of Z(OMe)—Arg(Mts)—Val—Tyr—OEt and added 3.6 ml. of 80% hydrazine aqueous liquor. The reaction mixture was left at room temperature overnight. The precipitated gel-like material was crushed with ethyl ether. After filtrating out, recrystallization from hot methanol-ethyl ether and ethanol yielded 4.1 g. (83% of theoretical amount) of the desired compound.

$R_{f1} = 0.58$.

(B-v) Synthesis of Z(OMe)—Arg(Mts)—Val—Tyr—Arg(Mts)—Pro—OH(9-13 position).

Into 80 ml. of methanol was dissolved 4.7 g. of Z(OMe)—Arg(Mts)—Pro—OBzl and added several drops of acetic acid. The reaction mixture was reduced with a catalytically effective amount of 10% paradium-carbon. The solvent was distilled away after filtration. If the removement of Z(OMe) as not completed, 2.9 ml. of anisole was added to the residue and the reaction mixture was treated with 12 ml. of TFA for 30 minutes while cooling with ice. After distilling away TFA at room temperature, the residue was washed with n-hexane by decantation and dried on KOH. Into 20 ml. of DMF was dissolved the residue and added 0.93 ml. of $Et_3N$ while cooling with ice. The resulting mixture was mixed at $-10°$ C. with a DMF solution of Z(OMe-)—Arg(MTs)—Val—Tyr—$N_3$ prepared from 5.26 g. of the hydrazide derivative thereof, 0.87 ml. of isoamylnitrate and 0.92 ml. of $Et_3N$ and added 0.93 ml. of $Et_3N$. The obtained reaction mixture was kept at $-10°$ C. for 24 hours to cause reaction and neutralized with two or three drops of acetic acid. After distilling away the solvent, the residue was dissolved in 5% $NaHCO_3$, washed with ethyl ether, converted to acid with citric acid and extracted with AcOEt. The resulting AcOEt phase was washed with 5% citric acid, 5% $NaHCO_3$ and NaCl-water and then dried on $Na_2SO_4$. After distilling away AcOEt, petroleum ether was added to the residue for crystallization.

Recrystallization from methanol-ether yielded 5.40 g. (67% of theoretical amount) of the desired compound.

$R_{f1} = 0.75$.

| Amino acid | Amino acid compositions | |
|---|---|---|
| | Found (molar ratio) | Calcd. (molar ratio) |
| Pro | 0.96 | 1 |
| Val | 1.10 | 1 |
| Tyr | 1.00 | 1 |
| Arg | 2.12 | 2 |
| mean recovery: 87% | | |

(C) Synthesis of Boc-Asp(OBzl)—Thr—Met—Arg(Mts)—Cys(MBzl)—Met—Val—Gly—OH(1-8 composition), M.W.: 1,404.718.

(C-i) Synthesis of Boc—Val—Gly—OBzl(7-8 position), M.W.: 364.43.

To AcOEt solution containing 6.55 g. of Boc—Val—OH and H—Val—OBzl prepared from 10.12 g. of the p-toluene sulfonate thereof and 4.2 ml. of Et$_3$N was added 7.42 g. of DCC while cooling with freezing mixture. The resulting mixture was kept at room temperature for 24 hrs. to cause reaction. After filtrating out the dicyclourea, the filtrate was washed with 5% citric acid, 5% Na$_2$CO$_3$ and NaCl-water and then dried on Na$_2$SO$_4$. After distilling away AcOEt, n-hexane was added to the residue for crystallization. Recrystallization from methanol-petroleum ether yielded 9.0 g. (82% of theoretical amount) of the desired compound.

$R_{f1}$=0.90, $R_{f4}$=0.38.

Elemental analysis for C$_{19}$H$_{28}$N: Calcd. (%): C: 62.62, H: 7.74, N: 7.69, Found (%): C: 62.80, H: 8.02, N: 7.65.

(C-ii) Synthesis of Z(OMe)—Cys(MBzl)—Met—OMe (5-6 position), M.W.: 486.636.

To 250 ml. of AcOEt solution containing 17.07 g. of Boc—Cys(MBzl)—OH and H—Met—OMe prepared from 9.99 g. of the hydrochloride thereof and 7 ml. of Et$_3$N was added 11.35 g. of DCC while cooling with freezing mixture. The resulting mixture was kept at room temperature for 24 hrs. to cause reaction. After filtrating out dicyclourea, the filtrate was washed with 5% citric acid, 5% Na$_2$CO$_3$ and NaCl-water and then dried on Na$_2$SO$_4$. After distilling away AcOEt, n-Hexane was added to the residue for crystallization.

Recrystallization from AcOEt-ether yielded 15.7 g. (65% of theoretical amount) of the desired compound.

$R_{f4}$=0.23, $R_{f3}$=0.89.

Elemental analysis for C$_{22}$H$_{34}$N$_2$O$_6$S$_2$: Calcd. (%): C: 54.30, H: 7.04, N: 5.76, Found (%): C: 54.29, H: 7.09, N: 5.76.

(C-iii) Synthesis of Z(OMe)—Thr—Met—OMe(2-3 position), M.W.: 428.494.

Into 200 ml. of dioxane was dissolved 10.0 g. of Z(OMe)—Thr—OH.DCHA (a salt of dicyclohexylamine) and 4.29 g. of HCl.H—Met—OMe and was added 4.89 g. of DCC while cooling with freezing mixture. The resulting mixture was kept at room temperature for 18 hrs. to cause reaction. After filtrating out dicyclourea and distilling away the solvent, the residue was dissolved into AcOEt, washed with 5% citric acid, 5% Na$_2$CO$_3$ and NaCl-water and then dried on Na$_2$SO$_4$. After distilling away AcOEt, ether was added to the residue for crystallization to give 8.50 g. (92% of theoretical amount) of the desired compound.

$R_{f1}$=0.60.

Elemental analysis for C$_{19}$H$_{28}$N$_2$O$_7$S: Calcd. (%): C: 53.25, H: 6.59, N: 6.54, Found (%): C: 53.23, H: 6.85, N: 6.68.

(C-iv) Synthesis of Z(OMe)—Thr—Met—N$_2$H$_3$(2-3 position), M.W.: 428.50.

Into 100 ml. of methanol was dissolved 4.3 g. of Z(OMe)—Thr—Met—OMe and added 5.7 ml. of 80% hydrazine aqueous liquor. The resulting mixture was left at room temperature overnight. After distilling away the solvent, ethanol was added to the residue for crystallization to give 4.10 g. (96% of theoretical amount) of the desired compound.

$R_{f1}$=0.56.

Elemental analysis for C$_{18}$H$_{28}$N$_4$O$_6$: Calcd. (%): C: 50.45, H: 6.59, N: 13.08, Found (%): C: 50.49, H: 6.67, N: 13.02.

| Amino acid | Amino acid compositions | |
|---|---|---|
| | Found (molar ratio) | Calcd. (molar ratio) |
| Thr | 1.06 | 1 |
| Met | 1.00 | 1 |
| mean recovery: 87% | | |

(C-v) Synthesis of Z(OMe)—Arg(Mts)—Cys(MBzl)—Met—OMe(4-6 position), M.W.: 889.098.

To 4.84 g. of Boc—Cys(MBzl)—Met—OMe was added 5.4 ml. of anisole. The resulting mixture was treated with 20 ml. of TFA for 60 minutes while cooling with ice. The obtained solution was added to n-hexane and washed by decantation. The resulting oily material was dried on KOH and dissolved into 30 ml. of DMF. To the resulting solution was added 1.4 ml. of Et$_3$N while cooling with ice and then mixed acid anhydride prepared from Z(OMe)—Arg(Mts)—OH from which was prepared 6.20 g. of the salt of cyclohexylamine thereof and 10 ml. of 1N HCl, 1.54 ml. of Et$_3$N and 1.58 ml. of isobutylchloroformate in 50 ml. of THF under anhydrous condition. The obtained reaction mixture was kept at −10° C. for 3 hrs. to cause reaction. After distilling away the solvent, the residue was dissolved into AcOEt, washed with 5% citric acid, 5% NaHCO$_3$ and NaCl-water and then dried on Na$_2$SO$_4$. After distilling away AcOEt, crystallization from ether and reprecipitation from methanol-ether repeated two times yielded 6.2 g. (70% of theoretical amount) of the desired compound.

$R_{f1}$=0.61.

(C-vi) Synthesis of Z(OMe)—Arg(Mts)—Cys(MBzl)—Met—N$_2$H$_3$(4-6 position), M.W.: 889.104.

Into 50 ml. of methanol was dissolved 4.4 g. of Z(OMe)—Arg(Mts)—Cys(MBzl)—Met—OMe and added 3 ml. of 80% hydrazine aqueous liquor. The resulting mixture was left at room temperature overnight to give gel-like material. The resulting material was crushed with ether and filtrated out. Reprecipitation from DMF-ethanol yielded 3.0 g. (68% of theoretical amount) of the desired compound.

$R_{f1}$=0.46.

Elemental analysis for C$_{40}$H$_{56}$N$_8$O$_9$S$_3$.0.5H$_2$O: Calcd. (%): C: 53.49, H: 6.40, N: 12.48, Found (%): C: 53.47, H: 6.34, N: 12.55.

(C-vii) Synthesis of Z(OMe)—Arg(Mts)—Cys(MBzl)—Met—Val—Gly—OH(4-8 position), M.W.: 1,031.254.

Into 50 ml. of methanol was dissolved 1.3 g. of Boc—Val—Gly—OBzl and added several drops of acetic acid. The resulting mixture was reduced with a catalytically effecting amount of 10% paradium-carbon for 3 hrs. After filtrating out, the solvent was distilled away. The residue was crushed with n-hexane. To the obtained white powder having an amount of about 1.06 g. was added 2.09 ml. of anisole and treated with 10 ml. of TFA for 45 minutes while cooling with ice. After distilling away TFA at room temperature, the residue was dried on KOH, dissolved in a mixture of 2 ml. of dimethylsulfoxide (hereinafter referred to as "DMSO") and 10 ml. of DMF and added 1.1 ml. of Et$_3$N while cooling with ice. The resulting mixture was mixed with a DMF solution of Z(OMe)—Arg(Mts)—Val—Tyr—N$_3$ prepared from 3.8 g. of Z(OMe)—Arg(Mts)—Val—Tyr—N$_2$H$_3$, 0.62 ml. of isoamylnitrate and 1.32 ml. of Et$_3$N and added 0.6 ml. of Et$_3$N to cause reaction at −10° C. for 36 hrs. After neutralizing the obtained mixture with a few drops of acetic acid and distilling away the solvent, citric acid was added to the residue and it was left for a while. The resulting precipitation was crushed with 5% citric acid and water and then dried. Precipitation from DMF-AcOEt was repeated two times to give 2.8 g. (69% of theoretical amount of the desired compound.

Elemental analysis for $C_{47}H_{66}N_8O_{12}S_3 \cdot H_2O$: Calcd. (%): C: 53.80, H: 6.53, N: 10.68, Found (%): C: 53.74, H: 6.52, N: 10.54.

| Amino acid | Amino acid compositions | |
|---|---|---|
| | Found (molar ratio) | Calcd. (molar ratio) |
| Gly | 1.00 | 1 |
| Cys | 0.79 | 1 |
| Val | 1.00 | 1 |
| Met | 0.90 | 1 |
| Arg | 0.98 | 1 |
| mean recovery: 87% | | |

(C-viii) Synthesis of Z(OMe)—Thr—Met—Arg(Mts)—Cys(MBzl)—Met—Val—Gly—OH(2-8 position), M.W.: 1,263.552.

To 480 mg. of Z(OMe)—Arg(Mts)—Cys(MBzl)—Met—Val—Gly—OH was added 0.6 ml. of anisole. The resulting mixture was treated with 3 ml. of TFA for 45 minutes while cooling with ice, added n-hexane, washed by decantation and then added ether to give a white powder. The obtained powder was dried on KOH, dissolved in 5 ml. of DMF and then added 0.055 ml. of Et$_3$N while cooling with ice. The obtained mixture was mixed with 15 ml. of DMF solution of Z(OMe)—Thr—Met—N$_3$ prepared from 254 mg. of Z(OME)—Thr—Met—N$_2$H$_3$, 0.094 ml. of isoamylnitrate and 0.18 ml. of Et$_3$N and added 0.055 ml. of Et$_3$N to cause reaction at $-10°$ C. for 24 hrs. After neutralization with a few drops of acetic acid and distilling away the solvent, 5% of citric acid was added to the residue. The obtained precipitate was crushed and washed with 5% citric acid and water, and then dried. Precipitation from DMF-AcOEt, further DMF-methanol yielded 430 mg. (90% of theoretical amount) of the desired compound.

$R_{f1} = 0.41$.

Elemental analysis for $C_{56}H_{82}N_{10}O_{15}S_4$: Calcd. (%): C: 53.23, H: 6.54, N: 11.09, Found (%): C: 53.34, H: 6.64, N: 10.79.

(C-ix) Synthesis of Boc—Asp(OBzl)—Thr—Met—Arg(Mts)—Cys(MBzl)—Met—Val—Gly—OH(1-8 position), M.W.: 1,404.718.

To 348 mg. of Z(OMe)—Thr—Met—Arg(Mts)—Cys(MBzl)—Met—Val—Gly—OH was added 0.3 ml. of anisole and treated with 1.5 ml. of TFA for 45 minutes while cooling with ice. The reaction mixture was added n-hexane, washed by decantation and then treated with ether to give white powder. The obtained powder was dried on KOH, dissolved in 3 ml. of DMSO and 3 ml. of DMF and then added 0.077 ml. of Et$_3$N and Boc—Asp(OBzl) while cooling with ice. The reaction mixture was kept at room temperature for 24 hrs. to cause reaction and neutralized with a few drops of acetic acid. After distilling away the solvent, the residue was added 5% citric acid for precipitation, crushed and washed with 5% citric acid and H$_2$O and then dried. The resulting material was added ethanol and stirred for 24 hrs. while most of the succinimide derivative was passed into ethanol to give 300 mg. (78% of theoretical amount) of the desired compound.

Elemental analysis for $C_{63}H_{93}N_{11}O_{17}S_4$: Calcd. (%): C: 53.86, H: 6.67, N: 10.97, Found (%): C: 53.46, H: 6.67, N: 10.78.

(D) Fragment Condensation.

(D-i) Synthesis of Z(OMe)—Arg(Mts)—Val—Tyr—Arg(Mts)—Pro—Cys(MBzl)—Trp—Gln—Val—OBzl(9-17 position), M.W.: 1,945.298.

To 0.85 g. of Boc—Cys(MBzl)—Trp—Gln—Val—OBzl was added 1.08 ml of 2% ethanedithiol-anisole and treated with 5.00 ml. of TFA at $-5°$ C. for 60 minutes in a stream of N$_2$ gas. The reaction mixture was added n-hexane and washed by decantation. The resulting residue was added ether to give white powder, crushed with 5% NaHCO$_3$ to give free amine composition and then washed with H$_2$O and ether. The resulting material was dried on KOH and dissolved in 10 ml. of DMF. To the obtained solution was added 1.22 g. of Z(OMe)—Arg(Mts)—Val—Tyr—Arg(Mts)—Pro—OH and 0.153 g. of N-hydroxy benzotriazole (hereinafter referred to as "HOBt") and then added 0.25 g. of DCC while cooling with freezing mixture to cause reaction at room temperature for 24 hrs. After dicyclourea was filtrated out, the solvent was distilled away keeping the temperature below 30° C. After the residue was added to AcOEt and 5% NaHCO$_3$, the resulting precipitate was filtrated out, washed while stirring in 5% citric acid and H$_2$O and dried. Reprecipitation from DMF-AcOEt and DMF-AcOEt+ethanol yielded 1.1 g. (56% of theoretical amount) of the desired compound.

$R_{f1} = 0.52$, $R_{f2} = 0.42$.

Elemental analysis for $C_{97}H_{125}N_{17}O_{20}S_3$: Calcd. (%): C: 59.89, H: 6.48, N: 12.24, Found (%): C: 60.10, H: 6.72, N: 11.96.

| Amino acid | Amino acid compositions | |
|---|---|---|
| | Found (molar ratio) | Calcd. (molar ratio) |
| Glx | 1.00 | 1 |
| Pro | 0.82 | 1 |
| Cys | — | 1 |
| Val | 2.17 | 2 |
| Tyr | 1.01 | 1 |
| Arg | 2.00 | 2 |
| Trp | — | 1 |
| mean recovery: 80% | | |

Trp was analysed with 4M methane sulfonate. Cys was analyzed after performic acid oxidation.

(D-ii) Synthesis of Boc—Asp(OBzl)—Thr—Met—Arg(Mts)—Cys(MBzl)—Met—Val—Gly—Arg(Mts)—Val—Tyr—Arg(Mts)—Pro—Cys(MBzl)—Trp—Gln—Val—OBzl(1-17 position protected [Gln$^{16}$]—GH—RH), M.W.: 3,167.846.

To 230 mg. of the compound obtained in (D-i) was added 0.254 ml. of 2% ethanedithiol-anisole and treated with 1.00 ml. of TFA at $-5°$ C. in a stream of N$_2$ gas. The resulting residue was added n-hexane, washed by decantation and treated with ether to give white powder.

The obtained powder was further washed with 5% NaHCO$_3$, H$_2$O and ether, dried on KOH and then dissolved in 5 ml. of DMF. To the resulting solution was added 166 mg. of Boc—Asp(OBzl)—Thr—Met—Arg(Mts)—Cys(MBzl)—Met—Val—Gly—OH and 21.7 mg. of HOBt. After stirring the reaction mixture was added 26.8 mg. of DCC while cooling with freezing mixture to cause reaction for 48 hrs. Furthermore, the reaction mixture was added 11 mg. of HOBt and 14 mg. of DCC to cause reaction for 48 hrs. After filtrating out dicyclourea, the solvent was distilled away keeping the temperature below 30° C. The residue was added $H_2O$ for precipitation, crushed and washed with 5% citric acid and $H_2O$ and then dried. After precipitation from DMF-methanol was repeated two times, the obtained 275 mg. of crude compound was dissolved in a small amount of DMF and then chromatographed on a column (3×75 cm., volume: 530 ml.) of Sephadex LH-20. Elution was effected with DMF and the main fraction was collected. After distilling away DMF keeping the temperature below 30° C., the residue was treated with $H_2O$ to give 220 mg. (59% of theoretical amount) desired compound as a white powder.

$R_{f1}=0.60$, $R_{f2}=0.55$.

| Amino acid | Amino acid composition | |
|---|---|---|
| | Found (molar ratio) | Calcd. (molar ratio) |
| Asp | 1.16 | 1 |
| Thr | 1.12 | 1 |
| Glx | 0.90 | 1 |
| Pro | 0.78 | 1 |
| Gly | 1.28 | 1 |
| Cys | — | 2 |
| Val | 3.01 | 3 |
| Met | 1.66 | 2 |
| Tyr | 0.88 | 1 |
| Arg | 3.00 | 3 |
| Trp | — | 1 | mean recovery: 78%

(E) Purification.

To 120 mg. of Boc—(1-17 position)—OBzl was added 0.33 ml. of m-cresol and 0.11 ml. of ethanedithiol and added 3.02 ml. of TFA solution of 1M trifluoromethanesulfonate-thioanisole while cooling with ice. The reaction mixture was treated at 0° C. for 3 hrs. to remove all protective groups. After the solvent was distilled away with vacuum pumps, the residue was added ether to give powder. After the powder was filtrated out, the residue was immediately dissolved in a small amount of water which was degassed and substituted with $N_2$ gas and the insoluble material was filtrated out. The obtained filtrate was diluted with 400 ml. of 0.01M ammonium acetate, pH 7.0 to give a concentration of 0.1 μmole/l and kept at room temperature for three days in a dark room for air oxidation. When it was confirmed by Ellman test that the absorbance at 412 nm. was reduced from 0.27 to 0.12 and kept constant, the diluted filtrate was adjusted to pH 5.0 with 5% acetic acid and lyophilized to give about 40 mg. of the crude [Gln$^{16}$]—GH—RH.

The crude [Gln$^{16}$]—GH—RH was suspended into a small amount of 1N acetic acid and centrifuged. The obtained supernatant was chromatographed on a column (3×95 cm, volume: 672 ml.) of Sephadex G-25 in which elution was effected with 1N acetic acid and every 4 ml.-column effluent were collected for purification. The obtained compound which was gel-filtrated was lyophilized, dissolved in 0.1N acetic acid and then centrifuged for removing insoluble materials. The resulting supernatant was chromatographed on a column of HPLC (μ Bondapak TM/C18). Elution was effected by means of a linear gradient obtained by 10% acetonitrile and 50% acetonitrile in 0.1% TFA for 30 minutes in a constant level device at a flow rate of 2 ml./minute (4 ml./minute for fractionating).

Figure 7:
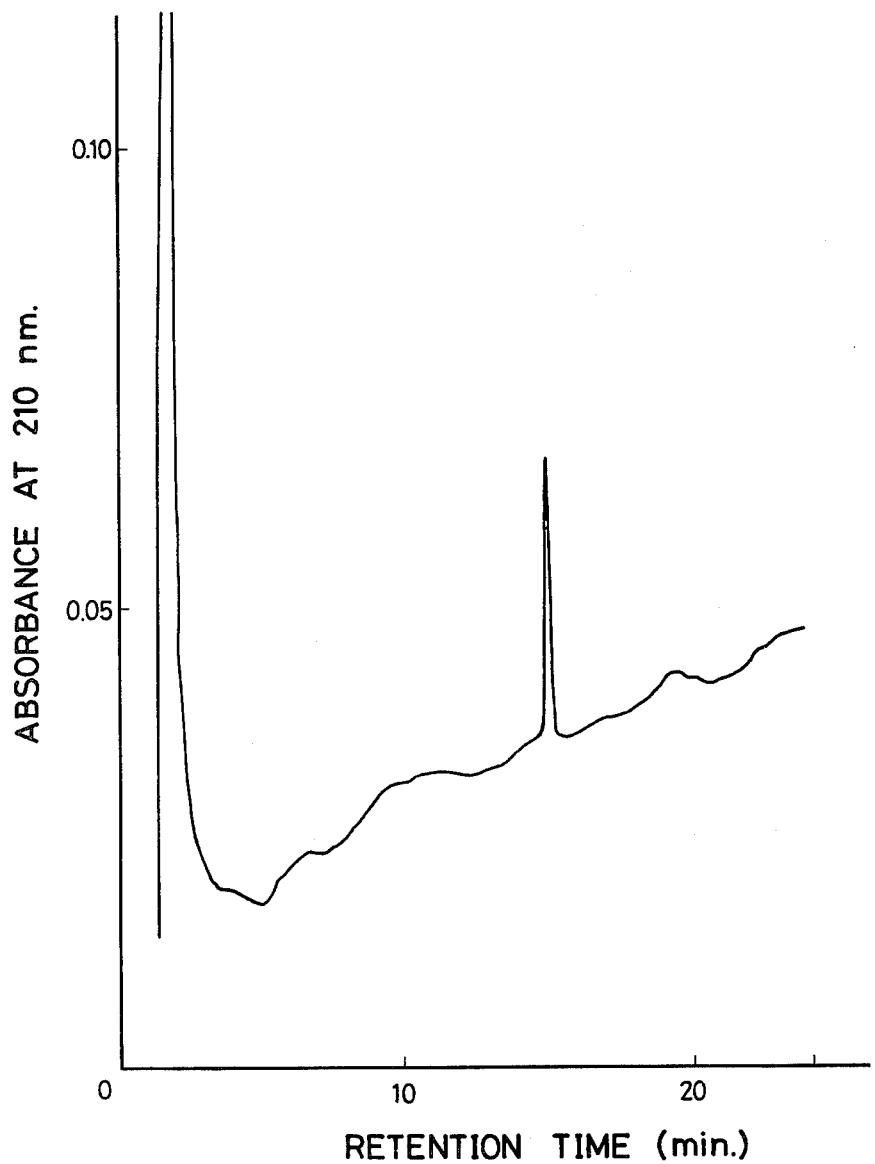
FIG. 7 represents an elution curve obtained by means of a HPLC in Example 2.

The resulting elution curve is shown in FIG. 7.

From FIG. 7, the purified peptide has a single peak in the HPLC and its retention time is extremely similar to that of the GH—RH obtained from salmon.

The physical properties of the peptide are as follows:

$R_f=0.44$, (carrier: Kiesel gel 60F2544 made by E. Merck G.A. developing solvent: n-butanol:AcOEt:acetic acid:water=1:1:1:1).

$[\alpha]D = -14.4°$ (C=0.1, $H_2O$).

| Amino acid | Amino acid compositions | |
|---|---|---|
| | Found (molar ratio) | Calcd. (molar ratio) |
| Asp | 1.08 | 1 |
| Thr | 1.00 | 1 |
| Glx | 1.00 | 1 |
| Gly | 1.14 | 1 |
| Cys | —* | 2 |
| Val | 3.03 | 3 |
| Met | 1.93 | 2 |
| Tyr | 1.00 | 1 |
| Arg | 3.00 | 3 |
| Trp | —* | 1 |
| Pro | 1.01 | 1 |

Cys and Trp cannot be detected in case of hydrolysing in 6N HCl.

ANALYTICAL EXAMPLE 9

[Carboxypeptidase P digestion]

In the amino acid analysis conducted after hydrolysis in 6N HCl, it cannot be determined whether Glu or Gln is detected. From the above reason C-terminal amino acid analysis with carboxypeptidase was carried out.

Into 150 μl. of 0.1N pyridine-acetate, pH 5.5 was dissolved about 4.4 μg. (about 2 nmoles) of the [Gln$^{16}$]—GH—RH obtained in Example 2 or the GH—RH obtained from salmon in Example 1 and added about 2 μl. of 1 mg./ml. $H_2O$ of carboxypeptidase P (Protein Research Foundation). The reaction mixture was incubated at 37° C. for 3 hrs.

After removing the solvent, the residue was dissolved into 300 μl. of 0.02N HCl and analysed on Hitachi 835-50 amino acid autoanalyzer (Hitachi Ltd.). The result are shown in Table 1. The carboxypeptidase P is an exopeptidase which attacks the C-terminal peptide bond to liberate single amino acids.

TABLE 1

| | [Gln$^{16}$]-GH-RH | | GH-RH from salmon | |
|---|---|---|---|---|
| Amino acid | Retention time (min.) | Molar ratio | Retention time (min.) | Molar ratio |
| Gln | 19.98 | 0.84 | 19.98 | —* |
| Glu | 23.42 | —* | 23.92 | 0.73 |
| Val | 41.88 | 1.02 | 41.88 | 0.89 |

*not detected

It is apparent from Table 1 that Gln is at second from the C-terminal in the [Gln$^{16}$]—GH—RH while Glu is at the same position as above in the GH—RH obtained from salmon.

The same results were obtained in case of employing carboxypeptidase A (Sigma Chemical Company) which easily liberates Gln but slightly liberates Glu. The reaction was carried out under the same condition as in the carboxypeptidase P except that pyridine-acetate, pH 7.8, was employed instead of pyridine-acetate, pH 5.5. The results are shwon in Table 2.

TABLE 2

| | [Gln$^{16}$]-GH-RH | | GH-RH from salmon | |
|---|---|---|---|---|
| Amino acid | Retention time (min.) | Molar ratio | Retention time (min.) | Molar ratio |
| Gln | 19.88 | 0.45 | 19.88 | —* |
| Glu | 23.40 | —* | 23.40 | 0.08 |
| Val | 41.88 | 0.79 | 41.88 | 0.67 |

From Table 2, Gln was detected with Val in the [Gln$^{16}$]—GH—RH while Glu was slightly detected compared with Val in the GH—RH obtained from salmon. Needless to say, Gln was not detected in the GH—RH obtained from salmon.

From the above reason, the 16-position of the synthesized GH—RH is proved to be Gln.

EXAMPLE 3

[Synthesis of [Glu$^{16}$]—GH—RH]

The procedure of Example 2 was repeated except that Glu was used as a starting material instead of Gln.

The obtained [Glu$^{16}$]—GH—RH has extremely similar physical properties and pharmacological activity those of the GH—RH obtained from salmon and [Gln$^{16}$]—GH—RH.

RECIPE EXAMPLE

[Injection solution]

Into 5 ml. of distilled and sterilized water were dissolved 0.1 mg. of peptide of the present invention and 50 mg. of glycine, and then the obtained solution was divided into ten vials and lyophilized for the storage. To the lyophilized mixture was added suitable amount of sterile saline to make an injection solution at the time of use.

PHARMACOLOGICAL TEST EXAMPLE 1

Small pieces of anterior pituitaries obtained from male Wistar Rats were placed on top of a column being an injection cylinder having one milimeter diameter packed with 0.3 to 0.5 ml. of Sephadex G 25 equilibrated with a Krebs-Ringer buffer solution containing 0.1% calf serum at a flow rate of 0.5 ml./min. On the column were chromatographed 1 ml. of a control solution (a Klebs-Ringer buffer solution), 1 ml. of 2 µg./ml. solution of TRH and 1 ml. of 2 µg./ml. solution of the GH—RH obtained in Example 1 in that order. The column effluent was collected in 1 ml.-fractions and each fraction was analyzed by means of a radioimmunoassay with an anti-rat GH antibody (NIH standard) to determine an amount of the released rat GH in the assay. The results are shown in Table 3.

TABLE 3

| Samples | Amount of Released Rat GH (ng./ml.) |
|---|---|
| Peptide of the invention | 350 |
| TRH | 300 |
| Control | 70 |

As shown in Table 3, in case of employing the peptide of the present invention, the amount of released GH was about five times that of the control and the same as that of TRH having a GH—RH like non-specific effect. The releasing manner, however, is specific. That is to say, the releasing manner of the present invention was sharp, while that of TRH was broad.

PHARMACOLOGICAL TEST EXAMPLE 2

[GH-releasing activity of GH—RH in vivo]

Male Wistar rats of 10 weeks old were used. The rats were anesthetized with pentobarbital administered intraperitoneally (i.p.) in a dosage of 50 mg./kg. and fixed. Silastic tube (Dow Corning 0.020 in I.D., by 0.037 in O.D.) cannula of 3.5 cm was inserted to the heart side of right jugular vein in the rat. In the rat with chronic vein-cannula in plant, the other side of the cannula was taken out by 3 cm. from backside of neck and fixed on outer layer of skin.

From the cannula was injected 0.5 ml. of 20 units/ml. heparin, and then the cannula was pluged with a stainless-steel wire stopper. The rats were subjected to injecting of GH—RH and blood-gathering under nonanesthetic condition on the next day. Chlorpromazine hydrochloride was administered i.p. before 4 hrs. of injection in a dosage of 2 mg./kg. Four rats (D to G) received injection from the cannula of 440 µg./kg. of GH—RH obtained from salmon in Example 1. Three rats (A to C) received physiological saline as a control.

From each rat, 0.5 ml. of blood was gathered before 15 minutes of injection and after 15, 30, 60, 120 and 180 minutes of injection.

The gathered blood was centrifuged at 2,000×g for 10 minutes. For measuring GH-releasing activity, the supernatant (plasma) was assayed by means of a radio immuno assay (hereinafter referred to as "RIA") according to a double antibody method (see C. A. Birge et al Endocrinology 81, p.195 (1967)). The RIA of rat GH was carried out by employing NIH kit. The results are shown in Table 4 and FIG. 8 in which symbols A to G described in Table 4 correspond to those described in FIG. 8.

TABLE 4

| Control GH Concentration Mean ± S.E. (µIU/ml.) | Time after injection (min.) | Control GH Concentration (µIU/ml.) | | |
|---|---|---|---|---|
| | | A | B | C |
| 7.403 ± 0.613 | −15 (before injection) | 8.63 | 6.77 | 6.81 |
| 14.680 ± 6.371 | 15 | 27.42 | 8.11 | 8.51 |
| 15.963 ± 8.650 | 30 | 33.26 | 7.02 | 7.61 |
| 20.020 ± 8.223 | 50 | 15.52 | 35.97 | 8.57 |
| 17.990 ± 8.190 | 120 | | 26.18 | 9.80 |
| 14.105 ± 3.585 | 180 | | 17.69 | 10.52 |

| GH Concentration Mean ± S.E. (µIU/ml.) | Time after injection (min.) | GH Concentration (µIU/ml.) | | | |
|---|---|---|---|---|---|
| | | D | E | F | G |
| 10.158 ± 1.482 | −15 (before injection) | 10.18 | 7.09 | 9.20 | 14.16 |
| 8.108 ± 0.427 | 15 | 8.53 | 7.91 | 7.01 | 8.98 |
| 10.813 ± 2.811 | 30 | 7.84 | 19.11 | 6.94 | 9.36 |
| 50.720 ± 42.160 | 60 | 7.50 | 177.19 | 8.18 | 10.01 |
| 85.248 ± 61.207 | 120 | 13.18 | 8.87 | 52.44 | 266.50 |
| 91.945 ± 32.735 | 180 | 90.20 | 33.46 | 183.79 | 60.33 |

Figure 8:
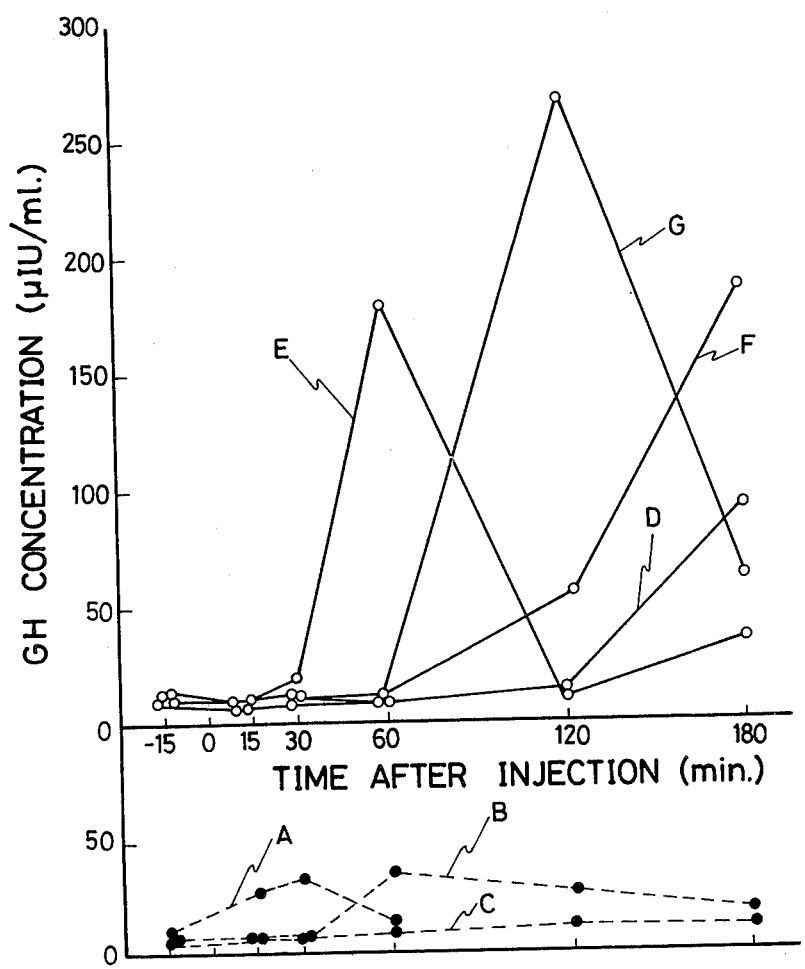
FIG. 8 is a graph showing a change with the lapse of time in GH-releasing activity of GH—RH in vivo obtained in Pharmacological Test Example 2.

From FIG. 8, the evident increase of GH concentration as to plasma was observed after 60 minutes of injection in the group receiving GH—RH in comparing with that observed in the control group even though difference between individual rats were observed.

In comparing with the GH-releasing activity of GH-releasing factor isolated from human pancreatic cancer (hereinafter referrd to as "hpGRF"), hpGRF showed increase of GH after 5 minutes of injection (see R. Guillemin et al, Science, 218, p.585 (1982)) while the GH—RH obtained from salmon showed increase of GH after one hour of injection. From the above results, it is confirmed that the GH-releasing effect of the GH—RH obtained from salmon does not effect directly on a pituitary but effects in a different manner.

PHARMACOLOGICAL TEST EXAMPLE 3

[GH-releasing activity of [Gln$^{16}$]—GH—RH in vivo]

The procedure of Pharmacological Test Example 2 was repeated except that six rats were used, respectively, as to the group receiving [Gln$^{16}$]—GH—RH and as to the group receiving physiological saline and the blood-gathering was carried out before 15 minutes of injection and after 15, 30, 60, 120, 180, 240 and 300 minutes, respectively, of injection.

Figure 9:
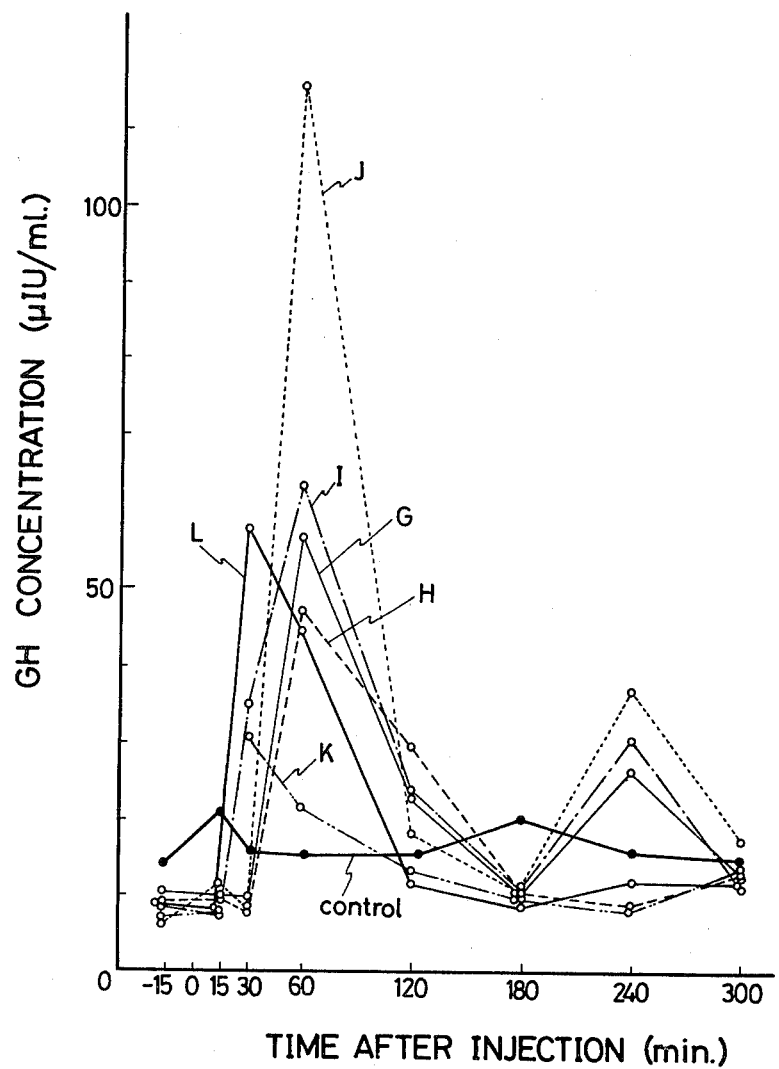
FIG. 9 is a graph showing a change with the lapse of time in GH-releasing activity of [Gln$^{16}$]—GH—RH in vivo obtained in Pharmacological Test Example 3.

The results are shown in Table 5 and FIG. 9 in which symbols G to L described in Table 5 correspond to those described in FIG. 9. In FIG. 9 date of the control group are described only by mean value.

TABLE 5

| Control GH Concentration Mean ± S.E. (μIU/ml.) | Time after injection (min.) | Control GH Concentration (μIU/ml.) | | | | | |
|---|---|---|---|---|---|---|---|
| | | A | B | C | D | E | F |
| 14.20 ± 2.98 | −15 (before injection) | 16.60 | — | 24.43 | 13.10 | 9.75 | 7.23 |
| 21.22 ± 3.40 | 15 | 33.60 | 25.98 | 13.23 | 17.03 | 24.95 | 12.55 |
| 16.33 ± 1.99 | 30 | 24.25 | 18.25 | 13.95 | 16.33 | 15.63 | 9.55 |
| 15.96 ± 2.57 | 60 | — | 8.63 | 17.08 | — | 17.50 | 20.63 |
| 15.98 ± 1.54 | 120 | 19.10 | 17.35 | 19.23 | 9.00 | 15.95 | 15.25 |
| 19.79 ± 2.64 | 180 | 26.40 | 23.60 | 11.38 | 24.95 | 19.95 | 12.48 |
| 14.57 ± 2.00 | 240 | 12.48 | 11.13 | 13.53 | 24.30 | 14.25 | 11.75 |

| GH Concentration Mean ± S.E. (μIU/ml.) | Time after injection (min.) | GH Concentration (μIU/ml.) | | | | | |
|---|---|---|---|---|---|---|---|
| | | G | H | I | J | K | L |
| 8.49 ± 0.62 | −15 (before injection) | 10.52 | 9.36 | 8.56 | 6.32 | 7.20 | 8.96 |
| 9.04 ± 0.68 | 15 | 10.04 | 9.76 | 7.20 | 11.52 | 7.64 | 8.08 |
| 24.87 ± 8.19 | 30 | 9.80 | 7.72 | 34.84 | 8.36 | 30.68 | 57.80 |
| 58.11 ± 12.84 | 60 | 56.52 | 47.00 | 63.40 | 115.36 | 21.48 | 44.88 |
| 19.70 ± 2.75 | 120 | 22.48 | 29.32 | 23.56 | 18.08 | 13.24 | 11.52 |
| 9.71 ± 0.34 | 180 | 10.08 | 9.72 | 10.56 | 10.24 | 9.48 | 8.20 |
| 20.00 ± 5.04 | 240 | 25.84 | 8.36 | 30.00 | 36.48 | 7.80 | 11.52 |
| 12.52 ± 0.92 | 300 | 12.36 | 12.08 | 10.32 | 16.64 | 12.96 | 10.76 |

From FIG. 9, the evident increase of GH concentration in plasma was observed from 30 to 60 minutes after injection in the group receiving [Gln$^{16}$]—GH—RH in comparing with that observed in the control group even though difference between individual rats were observed. Though the GH-releasing effect of the [Gln$^{16}$]GH—RH tends to appear earlier than that of the GH—RH obtained from salmon, it is clear that the [Gln$^{16}$]—GH—RH has a GH-releasing effect.

From the above results obtained in Pharmacological Test Examples 1 to 3, it is clear that the peptides of the present invention have a GH-releasing effect on foreign animals.

What is claimed is:

1. A peptide or the salt thereof having the structural formula (I):

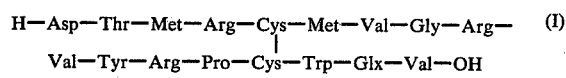

wherein Glx is Glu or Gln, and the following physical properties:
(1) Ultraviolet Absorption Spectrum: Max 280 nm.,
(2) Ehrlich reaction, Sakaguchi reaction and Pauly's reaction: positive,
(3) Basic,
(4) Soluble in water, methanol and acetic acid, slightly soluble in ethyl acetate, butyl acetate, ethyl ether, hexane, petroleum ether, benzene and chloroform, and
(5) white powder.

2. The peptide of claim 1, wherein said Glx is Glu.

3. The peptide of claim 1, wherein said Glx is Gln.

4. A composition for releasing growth hormone comprising an effective amount of a peptide of formula I or the salt thereof in an acceptable carrier, said peptide having the structural formula (I):

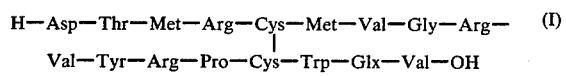

wherein Glx is Glu or Gln, and the following physical properties:
(1) Ultraviolet Absorption Spectrum: Max 280 nm.,
(2) Ehrlich reaction, Sakaguchi reaction and Pauly's reaction: positive,
(3) Basic,
(4) Soluble in water, methanol and acetic acid, slightly soluble in ethyl acetate, butyl acetate, ethyl ether, hexane, petroleum ether, benzene and chloroform, and
(5) white powder.

5. A composition of claim 4, wherein said Glx is Glu.

6. A composition of claim 4, wherein said Glx is Gln.

* * * * *